United States Patent [19]

Shalaby et al.

[11] Patent Number: 4,550,730
[45] Date of Patent: Nov. 5, 1985

[54] FLEXIBLE MONOFILAMENT SURGICAL SUTURES COMPRISING POLY(POLYMETHYLENE TEREPHTHALATE, ISOPHTHALATE OR CYCLOHEXANE-1,4-DICARBOXYLATE-CO-DIMERATE)

[75] Inventors: Shalaby W. Shalaby, Lebanon; Edgar S. Schipper, Cranford, both of N.J.

[73] Assignee: Ethicon, Inc., Somerville, N.J.

[21] Appl. No.: 555,746

[22] Filed: Nov. 28, 1983

Related U.S. Application Data

[63] Continuation-in-part of Ser. No. 328,351, Dec. 7, 1981, abandoned.

[51] Int. Cl.[4] ............... A61L 17/00; C08F 34/00
[52] U.S. Cl. ............................ 128/335.5; 128/1 R; 623/11; 623/66; 528/295
[58] Field of Search ............... 128/335.5, 1 R; 3/1; 528/295

[56] References Cited

U.S. PATENT DOCUMENTS

| | | | |
|---|---|---|---|
| 3,091,600 | 5/1963 | Caldwell et al. | 260/7.5 |
| 3,235,526 | 2/1966 | Cromell | 260/22 |
| 3,383,343 | 5/1968 | Mohajer et al. | 260/22 |
| 3,390,108 | 6/1968 | Keck et al. | 260/7.5 |
| 3,649,571 | 3/1972 | Keck | 260/22 |
| 3,795,644 | 3/1974 | Jackson, Jr. et al. | 260/22 |
| 3,954,689 | 5/1976 | Hoeschele | 260/22 |
| 4,224,946 | 9/1980 | Kaplan | 128/335.5 |
| 4,480,086 | 10/1984 | O'Neill | 528/295.5 |

FOREIGN PATENT DOCUMENTS

| | | |
|---|---|---|
| 649158 | 12/1964 | Belgium . |
| 1398551 | 3/1965 | France . |
| 994441 | 6/1965 | United Kingdom . |

OTHER PUBLICATIONS

Romanini et al., Polymer 21, 1092–1101 (1980).
Dobkowski, European Polymer Journal, vol. 17, pp. 1131–1144 (1981).

*Primary Examiner*—John Kight
*Assistant Examiner*—Kriellion Morgan
*Attorney, Agent, or Firm*—Leonard Kean

[57] ABSTRACT

A flexible monofilament surgical suture having unique handling and knot tying characteristics. Said suture comprises a drawn and oriented monofilament of a poly(polymethylene terephthalate, isophthalate or cyclohexane-1,4-dicarboxylate-co-dimerate), having the following combination of mechanical properties:
Tensile strength—at least about 60,000 psi
Knot strength—at least about 35,000 psi
Young's modulus—between about 80,000 and 280,000 psi
Elongation—from about 20% to 80%.

10 Claims, No Drawings

FLEXIBLE MONOFILAMENT SURGICAL SUTURES COMPRISING POLY(POLYMETHYLENE TEREPHTHALATE, ISOPHTHALATE OR CYCLOHEXANE-1,4-DICARBOXYLATE-CO-DIMERATE)

This is a continuation-in-part of our copending application Ser. No. 328,351, filed Dec. 7, 1981, now abandoned.

BACKGROUND OF THE INVENTION

The present invention relates to drawn and oriented surgical filaments and allied surgical products, and more particularly to strong, but flexible monofilament sutures having unique handling and knot tying characteristics. The novel sutures and surgical products of the present invention comprise an oriented copolymer consisting of recurring poly(polymethylene terephthalate, isophthalate or cyclohexane-1,4-dicarboxylate) and poly(polymethylene dimerate) units.

Many natural and synthetic materials are presently used as surgical sutures. These materials may be used as single filament strands, i.e., monofilament sutures, or as multifilament strands in a braided, twisted or other multifilament construction. Natural materials such as silk, cotton, linen, and the like, do not lend themselves to the fabrication of monofilament sutures and are accordingly generally used in one of the multifilament constructions.

Certain synthetic materials which are extruded in continuous lengths can be used in monofilament form. Common synthetic monofilament sutures include polypropylene, polyethylene and nylon. Such monofilament sutures are preferred by surgeons for many surgical applications due to their inherent smoothness and non-capillarity to body fluids.

Available synthetic monofilament sutures all suffer to a greater or lesser degree from one particular disadvantage, that is relative stiffness. Besides making the material more difficult to handle and use, suture stiffness or low compliance can adversely affect knot tying ability and knot security. It is because of the inherent stiffness of available monofilament sutures that many suture materials are braided or have other multifilament constructions with better handling, flexibility and conformity.

Most monofilament sutures of the prior art are also characterized by a low degree of compliance. This makes knot tying difficult and reduces knot security. In addition, the low compliance and limited ductility prevent the suture from 'giving' as a newly sutured wound swells, with the result that the suture may place the wound tissue under greater tension than is desirable, and may even cause some tearing, cutting or necrosis of the tissue.

The problems associated with the use of low compliance sutures in certain applications were recognized in U.S. Pat. No. 3,454,011, where it was proposed to fabricate a surgical suture composed of Spandex polyurethane. Such sutures, however, were too elastic and did not find general acceptance in the medical profession.

Recently issued U.S. Pat. No. 4,224,946 describes a monofilament suture with good flexibility and knot strength, which suture is composed of block polyetheresters which contain (1) a polymeric block of polyalkylene ethers and (2) a polymeric block of aromatic dicarboxylic acids or cycloaliphatic acids with short chain aliphatic or cycloaliphatic diols. Similar subject matter is disclosed in Belgian Pat. No. 880,486.

Copolyesters of aromatic diacids (e.g. terephthalic acid) and "dimer acids" of $C_{18}$ unsaturated fatty acids have been known for some time in the technical and patent literature.

Hoeschele [Angew.Makromol.Chem. 58/59, 229(1977)] as well as in U.S. Pat. No. 3,954,689 disclosed the preparation of thermoplastic PBT (polybutylene terephthalate)/dimerate systems for the generation of elastomeric films and molded articles which were largely unoriented. However, no reference was made to the conversion of these copolymers to oriented fibers, which would possess mechanical properties suitable for use as flexible monofilament sutures.

In connection with the Hoeschele U.S. Pat. No. 3,954,689, discussed above, all of the features stressed by Hoeschele relate to those that one would associate with rubbers ( and not drawn fibers) i.e., flexibility, abrasion, resistance, etc. and with coating materials and with materials suitable for molded articles. The fact that Hoeschele's materials are suitable for molding does not imply that they are necessarily suitable for spinning (for example, butyl rubber cannot be used to make fibers). Although Hoeschele covers a broad range with respect to his "hard" and "soft" components, which ratio encompasses the presently claimed ratio thereof, nevertheless there is no specific disclosure of the presently claimed ratio range. Accordingly, even if an attempt were to be made to produce fibers from the Hoeschele copolymers, there is no specific teaching by Hoeschele of the optimum ratio range found by the present applicant to be essential for the production of suitable surgical filaments and accordingly the Hoeschele disclosure is deficient in this regard.

In accordance with the present invention there is provided a drawn and oriented, flexible thermoplastic surgical filament which has an unusual combination of acceptable knot strength and high compliance, an integration of properties that is non-existent in commercial monofilament sutures. Accordingly, the two critical parameters required in accordance with the present invention are the Young's modulus (which is the reciprocal of compliance) and knot strength, the latter being the most important parameter. The range of compositions disclosed by Hoeschele in U.S. Pat. No. 3,954,689 for the "rubbery" material disclosed therein is broad, but absolutely no indication is provided by Hoeschele concerning any critical range of compositions which could provide a balance of good knot strength and high compliance, which is not surprising since his invention was totally unrelated to drawn fibers. For a useful surgical suture of common diameter such as size 3/0, it is critical that the knot strength be at least 35,000 psi. On the other hand, in a uniquely compliant useful surgical suture, the Young's modulus should be between about 80,000 and 280,000 psi. In this connection it was found, in accordance with the present invention, that a copolymer composition containing between 8 and 13 mole % of the dimerate component is absolutely essential in order to provide the unique combination of properties discussed above. The criticality of the particular compositions dependent upon the two parameters of Young's modulus and knot strength was further verified by preparing and testing a homopolymer (i.e., a polymer containing 0% of the dimerate), as well as a copolymer containing 84.275 mole % of the "hard" component and 15.725% of the "soft" dimerate component (which is the same as the copolymer prepared in accordance with Example I of the Hoeschele U.S. Pat. No. 3,954,689) in order to compare the properties thereof with the presently claimed range of 8–13 mole % of the dimerate component. The properties of the aforementioned hopolymer and copolymer known from the Hoeschele patent are set forth in present Example VI. Example I of the Hoeschele patent was selected for comparison purposes since the product thereof represents the closest composition, exemplified in Hoeschele, to that presently claimed, as a fiber-former.

As can be seen from the table in Example VI fibers prepared from both the Hoeschele copolymer X and the homopolymer Y possess acceptable and almost identical straight tensile strengths. Although the homopolymer Y has good knot strength, its compliance is unacceptable, for it is about 3 times as stiff as applicant's preferred suture which contains 10% of the "soft" component as indicated by samples 9–12 in Table II wherein the Young's modulus varies between 126,000 psi and 162,000 psi. Although the Hoeschele copolymer X has a low Young's modulus, it possesses a completely unacceptable knot strength (for a size 3/0 strand) of only 28,427 psi. Samples 9–12 of the present invention, as indicated in Table II herein, possess, on the other hand, knot strengths ranging between 39,000 psi and 41,000 psi. This difference between the knot strength of copolymer X and that of the presently claimed copolymer, is surprising, since the mole percentages of the "soft" dimerate components of the two chains in question are only slightly different. The selection of the minimum knot strength is in accordance with the USP requirements for nominal size 3/0 sutures. Specifically, the value of 35,750 psi is the intrinsic knot strength corresponding to the mean of the two values of intrinsic strength calculated using the "Average Knot-Pull Tensile Strength" and Minimum and Maximum Average Diameters for size 3/0 as found on page 714 of the fourth supplement of the USPXX Official Monograph [1983].

Data with respect to the homopolymer Y in Example VI herein is given in order to illustrate the fact that when the mole percentage of the "soft" component reaches 0 the resultant homopolymer is unacceptably stiff. It has been found, in accordance with the present invention that the mole percentage range of the "soft" component which provides the required properties of the present invention, is surprisingly narrow.

According to a number of patents [U.S. Pat. No. 3,390,108 (1968), U.S. Pat. No. 3,091,600 (1963) and British Pat. No. 994,441 (1965)], PET (polyethylene terephthalate) copolymers containing small amounts of dimerate moieties were spun into fibers which possessed superior dying properties. In accordance with U.S. Pat. No. 3,649,571, polyethylene terephthalate is rendered dyeable by incorporating therein the product of the reaction of a small amount of dimer acid with the sodium salt of isothionic acid. Since the processes of dye takeup and diffusion during conventional external dyeing, invariably take place in amorphous regions of a polymer, the observed enhancement of dyeability of the modified PET fibers may be attributed to a lowering of crystallinity by the dimerate structure. At the dimerate levels used in these compositions, the mechanical properties of the fibers are far from compatible with those applications which are sought for sutures, for at least their low compliance (or high Young's Modulus).

In the few instances in which higher concentrations of dimerate were incorporated into PET copolymers [Belgium Pat. No. 649,158 (1964), U.S. Pat. No. 3,383,343 (1968), and French Pat. No. 1,398,551 (1965)], the resulting fibers exhibited inferior tensile properties which rendered these products unsuitable as potential suture materials.

In view of the above discussion, the prior art holds little promise for the utilization of a polyester/dimerate polymer as basis for a suture material. Furthermore, since dimer acids are long chain branched molecules, the findings in the literature were not surprising, as theory and experience in the art of fiber science predict that branching exerts a deleterious effect on the tensile properties of the resulting fibers. The reason for this is (a) the inability of the branch to confer good tensile properties, which by its very nature can neither be easily oriented along the fiber axis nor contribute to the load bearing capacity of the fiber required to counteract mechanical stresses and (b) the steric interference posed by the branch to the main chain alignment during fiber orientation.

It is an object of the present invention to provide a novel flexible, thermoplastic monofilament suture or ligature of poly[polymethylene terephthalate, isophthalate or cyclohexane-1,4-dicarboxylate-co-dimerate], having a diameter of from about 0.01 to 1.0 mm and possessing unique and desirable physical properties. A further object of the present invention is to provide a filament which suffers practically no losses in physical properties as judged by a comparison of inherent viscosities and tensile strength before and after $Co^{60}$ sterilization (2.5 megarads). It is yet a further object of the present invention to provide a filament which possesses superior thermal oxidative stability as compared with more conventional types of low modulus thermoplastics such as those denoted as polyetheresters (this is because of the inherent instability of the latter). Another object is to provide a filament having improved dye retention, when utilizing dispersed-type dyes in a typical melt dying process. These and other objects will be made apparent from the ensuing description and claims.

SUMMARY OF THE INVENTION

The present invention relates to a drawn and oriented, flexible thermoplastic surgical filament, comprising a copolymer consisting essentially of a multiplicity of recurring A [poly(polymethylene terephthalate, isophthalate or cyclohexane-1,4-dicarboxylate)] and B [poly(polymethylene dimerate)] units having the following general formula:

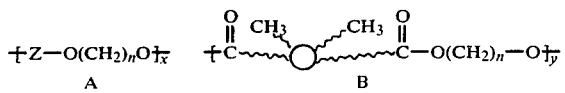

wherein—Z—represents a member selected from the group consisting of

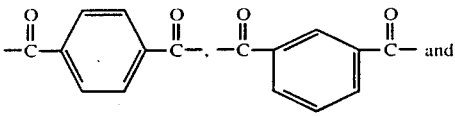 and

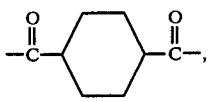

n is 4 to 8, x and y are numbers having average values, such that the A units comprise 87 to 92 mole percent, and the B units comprise 13 to 8 mole percent of the copolymer, and

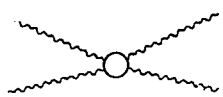

denotes a branched hydrocarbon chain containing from 24 to 32 carbon atoms, in which a size 3/0 strand of said filament has the following combination of mechanical properties:
Knot strength—at least about 35,000 psi
Tensile strength—at least about 60,000 psi
Young's modulus—between about 80,000 and 280,000 psi
Elongation—from about 20% to 80%

In accordance with the preferred embodiment of the present invention, Z is

and the following discussion will more fully describe such preferred embodiment.

The general structure of the copolymer used in forming preferred monofilament sutures of the present invention may be expressed as follows:

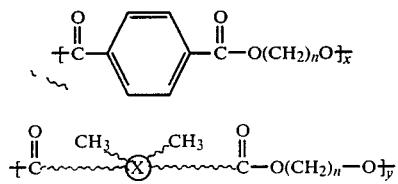

wherein

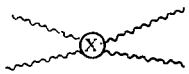

denotes a branched hydrocarbon chain containing 32 carbon atoms.

The structure belongs to the random copolymer type and x and y are integers, such that the poly(polymethylene terephthalate) units comprise 87 to 92 mole percent, and the poly(polymethylene dimerate) units comprise 13 to 8 mole percent of the copolymer; and n is 4 to 8 and is preferably 4.

The preferred composition range, for fiber formation, is 88–90 mole percent of the poly(polymethylene terephthalate) units.

Monofilament sutures of the present invention (having a size 3/0 strand) are preferably characterized by the following combination of mechanical properties:
Knot strength—35,000 to 40,000 psi
Tensile strength—60,000 to 80,000 psi
Young's modulus—less than about 165,000 psi
Elongation—from about 35% to 50%

Sutures possessing the above characteristics may be prepared by melt extrusion, forming a continuous filamentary strand, and drawing the extruded filament to obtain the desired suture properties.

Monofilament sutures having physical properties in accordance with the present invention are particularly useful in many surgical procedures where the suture is used to close a wound which may be subject to later swelling or change in position. The combination of low Young's modulus and high elongation provides the suture with an appreciable degree of ductility and high compliance under low applied force. As a result, the suture is able to "give" to accommodate swelling in the wound area. In addition, the ductility and high tensile strength of the suture allow the suture to stretch during knot tie-down so that the knot "snugs down" for improved tying ability and knot security with a more predictable and consistent knot geometry regardless of variations in suture tying technique or tension.

Within the scope of the present invention is a filament as described above having a surgical needle attached to at least one end and useful as a surgical suture. Also within the scope of the present invention is such a filament or surgical suture in a sterile condition, and in addition such filament or sterile suture, packaged in a sterile enclosure. Also within the scope of the present invention is a method of closing a wound by approximating and securing the wound tissue with a filament or surgical suture of the present invention.

DESCRIPTION OF THE PREFERRED EMBODIMENTS

The polymers used in the preferred embodiments of the present invention are prepared by the polycondensation of dimethyl terephthalate, dimer acid, or preferably its diisopropyl ester and a polymethylene diol (n=4 to 8, and preferably 4).

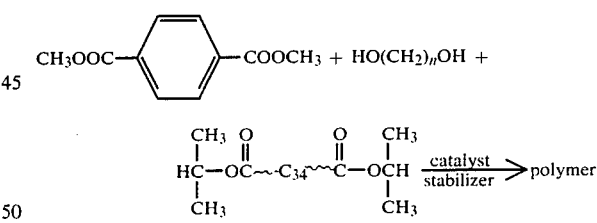

The preferred parent dimer acid of the diisopropyl ester utilized in the polymerizations is derived from high purity oleic acid and is formed by a clay catalyzed high pressure dimerization of the oleic acid in the presence of water. The mechanism of formation of the dimer acid is probably free radical in nature and the product is believed to consist of a mixture of acyclic unsaturated $C_{36}$ acids. The unsaturated materials are then hydrogenated and the dimer ester used in the present polymerizations possesses a slight degree of unsaturation as evidenced by an Iodine number of 5. In addition to the $C_{36}$ acids that make up the dimer acid there is present some monofunctional acid (iso-stearic) and a certain quantity of trifunctionality in terms of a "trimer ($C_{54}$) acid." The former may act as a chain terminator and the latter as crosslinking agent. Detailed structures of the $C_{36}$ components of the dimer acid have not been elucidated as yet and the diacid is sometimes represented graphically as shown below (with four almost equal branches).

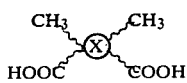

The reaction may be run in the absence or preferably in the presence of stabilizers taken from the types of hindered phenols or secondary aromatic amines. An example of the former is Irganox 1098 sold by Ciba-Geigy [N,N'-hexamethylene bis(3,5-ditert-butyl-4-hydroxy hydrocinnamide)] and an example of the latter is Naugard 445 sold by Uniroyal [4,4'-bis($\alpha,\alpha$-dimethylbenzyl)diphenyl amine)]. Oxides and alkoxides of numerous polyvalent metals may be employed as catalysts. A preferred catalyst for the polymerization is a mixture of 0.1 % tetrabutyl orthotitanate and 0.005 % magnesium acetate (percentages based on total charge weight). If a dyed end product is desired a compatible dye such as, for instance, D&C Green #6 can be added in suitable concentrations based on expected polymer yield.

The polymerization is run in two stages. In the first stage, run under nitrogen at temperatures ranging from 160° to 250° C., polycondensation via transesterification and esterification occurs resulting in oligomeric chains. These are converted to materials having a high degree of polymerization in the subsequent step run at 240° to 255° C., at pressures of less than 1 mm of mercury.

The resulting polymers exhibit inherent viscosities (measured in hexafluoroisopropyl alcohol) of 0.6 to 1.3. The Tm of the polymers, depending on composition, varies from 190° to 210° C. Apparent viscosities at suitable extrusion temperatures vary from $2 \times 10^3$ to $9 \times 10^3$ poise. A summary of polymer properties is given in Table I.

The polymers may readily be extruded in a ram type extruder, such as, an Instron capillary rheometer, at temperatures usually exceeding the polymer Tm by 10° to 50° C. The resulting extrudate may be drawn, usually in a two-stage process using either two consecutive heated glycerine baths or a hot shoe followed by a subsequent glycerine bath. The draw ratio may vary from about 400 to 700%.

The oriented fibers exhibit properties that are quite unexpected. Size 3/0 strands possess knot tensiles in the $35-40 \times 10^3$ psi range, straight tensiles in the $60-80 \times 10^3$ psi range and a Young's modulus of less than $150 \times 10^3$ psi. Elongations range from 35 to 50%.

In summary, the polymers described lend themselves to ready extrusion and drawing to strong and supple fibers which are useful as flexible monofilament sutures.

A survey of fiber properties is shown in Table II.

Both stabilized and unstabilized fibers, upon $Co^{60}$ sterilization (2.5 megarads) suffer practically no losses in physical properties as judged by a comparison of inherent viscosities and tensile strength before and after sterilization. The unexpected retention of physical properties revealed by the unstabilized fibers presents a distinct advantage of the present invention over prior art.

GENERAL POLYMERIZATION PROCEDURE

The desired amounts of dimethyl terephthalate, diisopropyl dimerate (obtained from Emery Industries as Emerest 2349), a 1.3 to 2.0 molar excess of a polymethylene diol and a given stabilizer are placed under nitrogen into a dry reactor fitted with an efficient mechanical stirrer, a gas inlet tube and a takeoff head for distillation. The system is heated under nitrogen to 160° and stirring is begun. To the homogeneous stirred solution the required amount of catalyst is added. The mixture is stirred and heated under nitrogen for given time periods at 190° C. (2-4 hours) and 220° C. (1-3 hours). The temperature is subsequently raised to 250° to 255° C. and over a period of 0.4–0.7 hours, the pressure is reduced in the system to below 1 mm/Hg (preferably in the range of 0.05 mm to 0.1 mm). Stirring and heating under the above conditions is continued to the completion of the polymerization. The endpoint is determined by either(a) estimating visually the attainment of maximum melt viscosity, (b) measuring inherent viscosity or melt indices of samples removed from the reaction vessel at intermediate time periods, and (c) using a calibrated torquemeter immersed into the mixture. In practice, depending on the terephthalate/dimerate ratio, in vacuo reaction times vary from 2 to 13 hours.

At the end of the polymerization cycle the hot mixture is equilibrated with nitrogen and allowed to cool slowly. The reaction product is isolated, chilled in liquid nitrogen and ground. The ground chips are dried at 80° to 110° C. for 8 to 16 hours under vacuum of 1 mm or less and subsequently submitted for extrusion.

GENERAL EXTRUSION PROCEDURE

Extrusion through the Instron Rheometer is geared towards producing an extrudate which upon drawing ($5 \times$ to $7 \times$ ratio) yields a fiber in the 8–10 mil diameter range (size 3/0 suture). The polymers are packed at 110° to 130° C. in the extrusion chamber and extruded after a dwell time of 9 to 15 minutes through a 40 mil die. The ram speed is 2 cm/minute. Extrusion temperatures depends both on the polymer Tm and on the melt viscosity of the material at a given temperature; usually extrusion proceeds at temperatures of 10° to 50° C. above the Tm. Die swells of up to 40% are experienced by usually are much smaller (5–20%); the extrudate is taken up at a speed of 18 feet per minute.

GENERAL DRAWING PROCEDURE

The extrudate (diameter range, 19–22 mm) is passed through rollers at an input speed of four feet per minute onto a hot shoe or into a draw bath varied from 50° to 100° C. Draw ratio in this first stage of operation vary from $5 \times$ to $6 \times$. The drawn fibers are placed over another set of rollers into a glycerine annealing bath (second stage) kept at temperatures ranging from 70° to 95° C. Draw ratios for the second stage operation vary from $1.1 \times$ to $1.25 \times$. Finally, the fiber is passed through a water wash bath and taken up on a spool.

In the following examples inherent viscosity (ninh) is obtained for polymer solutions in hexafluoro-2-propanol (HFIP) (1 g./1). The infrared spectra are obtained for polymer films cast from $CHCl_3$ or HFIP. The NMR spectra are recorded for polymer samples in solution in 60/40 hexafluoroacetone sesquideuterium oxide. The glass transition (Tg), crystallization (Tc) and melting (Tm) temperatures of the polymers in nitrogen are recorded, using a D.S.C. (differential scanning calorimetry) apparatus. The percent crystallinity is determined by X-ray. A hot-stage microscope is used to determine the melting behaviour of the polymers. Fiber tensile properties are measured on an Instron, Model No. 1122.

Steel faced jaws are used throughout. For the measurement of the Young's modulus, line contact jaws are applied. For straight tensile and moduli measurements a speed of 100 mm/min., a chart speed of 200 mm/min. and a gauge length of 12 cm is employed. For knot tensiles the above parameters are 100 mm/min., 100 mm/min. and 5 cm, respectively.

EXAMPLE I

The following materials are placed in a nitrogen glove box into a flamed, vacuum dried two-necked round bottom flask fitted with a stainless steel paddle shaped stirrer:

50.8 g. dimethyl terephthalate (0.2618 M)
40.2 g. 1,4-butanediol (0.4472 M)
23.5 g. diisopropyl dimerate (Emerest 2349; 0.0363 M)
0.8 g. 4,4'-bis($\alpha,\alpha$-dimethylbenzyl)diphenylamine
0.24 g. D&C Green #6

The open neck is fitted with a rubber septum, the flask and stirrer assembly is removed from the glove box, attached to an efficient mechanical stirrer and placed into an oil bath heated at 160° C. After several minutes, the reaction mixture liquifies and mechanical stirring is started. The catalyst (1.0 ml) consisting of 0.1% tetrabutyl orthotitanate and 0.005% magnesium acetate (percentages based on total charge weight) dissolved in a mixture of methanol and butanol is added through the septum to the reaction via a syringe. The septum is replaced by a short distilling head fitted with a receiver and a nitrogen inlet nozzle. The reaction mixture is heated under nitrogen at 190° C. for 3 hours and at 220° C. for 2 hours. As the methanol distillation ceases, the reaction temperature is increased to 250° C., the receiver containing the distillate is replaced by an empty flask and gradually, over a period of 30 minutes, the pressure in the reaction setup is reduced to 0.08 mm. The mixture is heated at this pressure and at 250° C. for 4 hours. The hot viscous mass is equilibrated with nitrogen and allowed to cool to room temperature. The polymer is isolated, chilled and then ground. The polymer chips are dried for 8 hours under a good vacuum and a temperature of 80° C. Properties of the polymer and of others prepared by similar reaction schemes are shown in Table I (see sample #6 for above-described polymer).

EXAMPLE II

The procedure of Example I is followed, in all respects with the one exception that a like quantity of dimethyl isophthalate is substituted in place of the dimethyl terephthalate used in the initial reaction mixture. The final product is a poly(tetramethylene dimerate coisophthalate) polymer.

EXAMPLE III

The procedure of Example I is followed in all respects, with the one exception that 52.4 g. of dimethyl cyclohexane-1,4-dicarboxylate is substituted in place of the 50.8 g. of the dimethyl terephthalate used in the initial reaction mixture. The final product is a poly(tetramethylene dimerate co-cyclohexane-1,4-dicarboxylate) polymer.

EXAMPLE IV

Ten grams of the copolymer described in Example I are packed at 150° C. into the extrusion chamber of an Instron Rheometer and after 15 minutes of dwell time the sample is extruded at a ram speed of 2 cm/min., a shear rate of 212.6 sec$^{-1}$ and a temperature of 250° C. The resulting melt viscosity is found to be 6178 poise. The takeup speed of the extrudate is 18 ft/min. and the extrudate is quenched in ice water. The diameter of extrudate is 21.0 mils.

The extrudate is drawn at 5× over a hot shoe held at a temperature of 99° C. and at 1.2× through a glycerine bath kept at 95° C. The fiber is pulled through a water bath (room temperature) to remove the glycerine and taken up on a spool. The draw tension for both the first drawing stage is 420 g. and for the second stage 380 g.; the total draw ratio is 6.0×. Tensile data for fibers obtained in this and other runs are shown in Table II.

EXAMPLE V

Fibers prepared from polymer #9 (Table I) are strung under a tension of 50 g. on an adjustable annealing rack. The adjustable bar is lowered about 10% to allow the fibers to relax freely. After 16 hours the adjustable bar is raised to a height which is sufficient to straighten the fibers without imparting any tension (0% relaxation). The fibers are subjected to one hour of heating at 110° C. and then cut off the annealing rack. Fibers annealed in this manner, upon exposure to free shrinkage (60° C./2.5 hours) shrink 2.3% as opposed to 15.6% for unannealed strands.

EXAMPLE VI

Copolymer X, which is the poly(tetramethylene dimerate-co-terephthalate) of Example I of the Hoeschele U.S. Pat. No. 3,954,689 was prepared, the molar monomer ratio [dimerate/terephthalate] being 15:725/84:275 and the poly.ninh at 25° C. in HFIP being 1.32.

In addition, homopolymer Y, which comprises poly(-tetramethylene terephthalate) [PBT] was prepared, the polyninh at 25° C. in HFIP being 1.52.

Polymers X and Y were subjected to extrusion in the same manner as indicated in Example IV, but the extrusion and orientation conditions were as follows:

A 40 mil. die was used and the shear rate was 212.6 sec$^{-1}$

| | | Copolymer X | Homopolymer Y |
|---|---|---|---|
| 1. | Extrusion Conditions | | |
| | Temperature | 240° C. | 250° C. |
| | $\alpha_{app}$, sec$^{-1}$ | 212.6 | 212.6 |
| | $\eta_{app}$, poise | 10,207 | 8,273 |
| 2. | Draw Ratio | 4× at 72° C. | 4× at 71° C. |
| | | 1.2× at 90° C. | 1.25 at 90° C. |
| 3. | Tensile Properties | | |
| | Tensile strength | 71,657 psi | 70,011 psi |
| | Knot strength | 28,427 psi | 64,958 psi |
| | Elongation | 62% | 32% |
| | Young's Modulus | 36,266 psi | 398,953 psi |

TABLE I

SYNTHESIS AND PROPERTIES OF POLY(TETRAMETHYLENE DIMERATE CO TEREPHTHALATE) POLYMERS

| Sample No. | Monomer Ratio* D/T | Stabilizer Type** | % D & C Green #6 (by wt.) | Polymerization Reaction Scheme Temp. °C. | Pressure mm Hg | Time Hours | Poly.$\eta$inh at 25° C. in HFIP | M.p. °C. (Microscopy) | Tm °C. |
|---|---|---|---|---|---|---|---|---|---|
| 1 | 13/87 | Naugard 445 (1%) | 0 | 160 | atm.$N_2$ | 0.2 | 0.90 | Not Available | Not Available |
| | | | | 190 | " | 3.0 | | | |
| | | | | 220 | " | 2.5 | | | |
| | | | | 250 | " | 1.5 | | | |
| | | | | 250 | 0.05 | 5.0 | | | |
| 2 | 13/87 | Naugard 445 (1%) | 0 | 160 | atm.$N_2$ | 0.2 | 0.98 | 195–197 | 196 |
| | | | | 190 | " | 3.0 | | | |
| | | | | 220 | " | 2.5 | | | |
| | | | | 250 | " | 1.5 | | | |
| | | | | 250 | 0.05 | 2.0 | | | |
| 3 | 13/87 | Naugard 445 (1%) | 0 | 160 | atm.$N_2$ | 0.2 | 0.90 | 195–196 | 195 |
| | | | | 190 | " | 3.0 | | | |
| | | | | 220 | " | 2.5 | | | |
| | | | | 250 | " | 1.5 | | | |
| | | | | 250 | 0.05 | 2.0 | | | |
| 4 | 13/87 | Naugard 445 (1%) | 0.3 | 160 | atm.$N_2$ | 0.2 | 1.17 | 197–199 | 194 |
| | | | | 190 | " | 3.0 | | | |
| | | | | 220 | " | 2.5 | | | |
| | | | | 250 | " | 1.5 | | | |
| | | | | 250 | 0.05 | 4.0 | | | |
| 5 | 12/88 | Naugard 445 (1%) | 0.3 | 160 | atm.$N_2$ | 0.2 | 0.96 | 197–198 | 199 |
| | | | | 190 | " | 3.0 | | | |
| | | | | 220 | " | 2.0 | | | |
| | | | | 250 | 0.05 | 13.0 | | | |
| 6 | 12/88 | Naugard 445 (1%) | 0.3 | 160 | atm.$N_2$ | 0.2 | 1.21 | 197–198 | 199 |
| | | | | 190 | " | 3.0 | | | |
| | | | | 220 | " | 2.0 | | | |
| | | | | 250 | 0.05 | 4.0 | | | |
| 7 | 12/88 | Naugard 445 (1%) | 0 | 160 | atm.$N_2$ | 0.2 | 1.00 | 198–200 | 203 |
| | | | | 190 | " | 2.5 | | | |
| | | | | 220 | " | 3.0 | | | |
| | | | | 250 | 0.05 | 8.0 | | | |
| 8 | 11/89 | Naugard 445 (1%) | 0 | 160 | atm.$N_2$ | 0.2 | 0.63 | 203–208 | 204 |
| | | | | 190 | " | 3.5 | | | |
| | | | | 220 | " | 1.8 | | | |
| | | | | 250 | " | 1.5 | | | |
| | | | | 250 | 0.05 | 5.3 | | | |
| 9 | 10/90 | Naugard 445 (1%) | 0 | 160 | atm.$N_2$ | 0.2 | 1.15 | Not Available | Not Available |
| | | | | 190 | " | 3.0 | | | |
| | | | | 220 | " | 2.0 | | | |
| | | | | 250 | 0.05 | 7.5 | | | |
| 10 | 10/90 | Naugard 445 (1%) | 0.3 | 160 | atm.$N_2$ | 0.2 | 1.06 | 202 | 203 |
| | | | | 190 | " | 3.0 | | | |
| | | | | 200 | " | 2.0 | | | |
| | | | | 250 | 0.05 | 5.0 | | | |
| 11 | 10/90 | None | 0.3 | 160 | atm.$N_2$ | 0.2 | 1.08 | 202–203 | 202 |
| | | | | 190 | " | 3.0 | | | |
| | | | | 220 | " | 2.0 | | | |
| | | | | 250 | 0.08 | 4.0 | | | |
| 12 | 10/90 | Irganox 1098 (0.25%) | 0.3 | Conditions same as in Sample 11. | | | 1.24 | 202–203 | 205 |

*D = dimerate moiety; T = terephthalate moiety.
**Naugard 445: 4,4'bis($\alpha,\alpha$-dimethylbenzyl)diphenyl amine Irganox 1098: N,N'—hexamethylene bis(3,5-ditert-butyl-4-hydroxyhydrocinnamide)

TABLE II

EXTRUSION AND DRAWING CONDITIONS AND
ULTIMATE TENSILE PROPERTIES FOR FIBER DERIVED FROM
DIMERATE CO TEREPHTHALATE) POLYMERS

| Sample No. | Extrusion Conditions T °C. | Extrusion Conditions $\eta_{app}$ (poise) | Drawing Conditions Ratio 1st Stage | Drawing Conditions Ratio 2nd Stage | Drawing Conditions T °C. 1st Stage | Drawing Conditions T °C. 2nd Stage | Dia. (mil) | Knot (psi × $10^{-3}$) | Straight (psi × $10^{-3}$) | % Elongation | Y.M. (psi × $10^{-3}$) |
|---|---|---|---|---|---|---|---|---|---|---|---|
| 1 | 215 | 5587 | 5× | 1.3× | 52 | 75 | 9.2 | 35.1 | 69.8 | 49 | 79.6 |
| 2 | 210 | 5050 | 6× | 1.08× | 85 | 92 | 8.6 | 32.5 | 74.0 | 47 | 79.2 |
| 3 | 210 | 5050 | 6× | 1.08× | 85 | 92 | 8.6 | 35.3 | 67.0 | 42 | 82.3 |
| 4 | 230 | 7682 | 5× | 1.1× | 96 | 95 | 9.5 | 36.3 | 75.8 | 43 | 108.5 |
| 5 | 225 | 6124 | 5× | 1.2× | 99 | 95 | 9.7 | 35.5 | 71.2 | 55 | 60.0 |
| 6 | 250 | 6178 | 5× | 1.2× | 99 | 95 | 9.0 | 40.6 | 81.4 | 41 | 117.2 |
| 7 | 215 | 7198 | 5× | 1.15× | 85 | 92 | 9.1 | 41.2 | 70.9 | 40 | 134.2 |
| 8 | 215 | 1128 | 6× | 1.17× | 52 | 72 | 8.2 | 37.3 | 66.7 | 35 | 141.2 |
| 9 | 220 | 9616 | 5× | 1.2× | 85 | 90 | 9.1 | 38.7 | 82.1 | 42 | 147.7 |
| 10 | 215 | 6285 | 5× | 1.25× | 79 | 79 | 9.2 | 43.8 | 70.3 | 40 | 162.2 |
| 11 | 210 | 7735 | 5× | 1.25× | 82 | 79 | 9.4 | 39.9 | 57.3 | 37 | 125.8 |
| 12 | 235 | 8541 | 5× | — | 91 | — | 9.8 | 41.1 | 62.6 | 48 | 138.9 |

The poly(polymethylene terephthalate, isophthalate or cyclohexane-1,4-dicarboxylate-co-dimerate) used in accordance with the present invention may be spun as multifilament yarn and woven or knitted to form sponges or gauze, (or nonwoven sheets may be prepared) or used in conjunction with other compressive structures as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged kidney, liver and other abdominal organs, protecting damaged surface areas such as abrasions, particularly major abrasions, or areas where the skin and underlying tissues are damaged or surgically removed.

In more detail, the surgical and medical uses of the filaments of the present invention include, but are not necessarily limited to:

Knitted products, woven, or nonwoven including velours a. burn dressings
b. hernia patches
c. medicated dressings
d. fascial substitutes
e. gauze, fabric, sheet, felt or sponge for liver hemostasis
f. gauze bandages In combination with other components a. arterial graft or substitutes
b. bandages for skin surfaces
c. burn dressings (in combination with polymeric films)

We claim:

1. A drawn and oriented, flexible thermoplastic surgical filament, comprising a copolymer consisting essentially of a multiplicity of random recurring A [poly(-polymethylene terephthalate, isophthalate or cyclohexane-1,4-dicarboxylate)] and B [poly(polymethylene dimerate)] units having the following general formula:

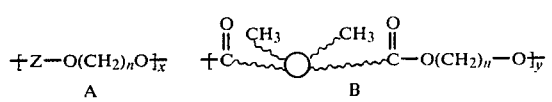

wherein—Z—represents a member selected from the group consisting of

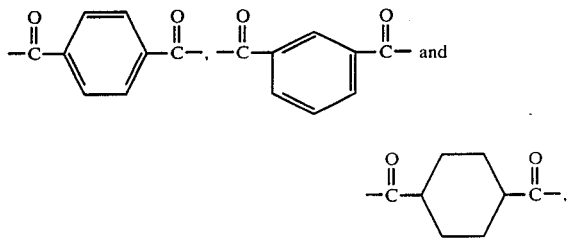

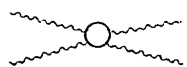

n is 4 to 8, x and y are numbers having average values such that the A units comprise 87 to 92 mole percent, and the B units comprise 13 to 8 mole percent of the copolymer, and denotes a branched hydrocarbon chain containing from 24 to 32 carbon atoms, in which a size 3/0 strand of said filament has the following combination of mechanical properties:

Knot strength—at least about 35,000 psi
Tensile strength—at least about 60,000 psi
Young's modulus—between about 80,000 and 280,000 psi
Elongation—from about 20% to 80%

2. A drawn and oriented, flexible thermoplastic surgical filament comprising a copolymer consisting essentially of a multiplicity of random recurring poly(-polymethylene terephthalate) and poly(polymethylene dimerate) units having the following general formula:

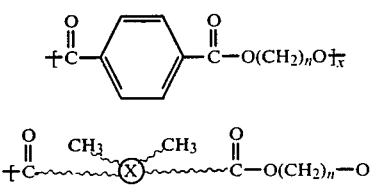

wherein n is 4, x and y are numbers having average values, such that the poly(polymethylene terephthalate) units comprise 87 to 92 mole percent, and the poly(-polymethylene dimerate) units comprise 13 to 8 mole percent of the copolymer, and denotes a branched hydrocarbon chain containing 32 carbon atoms, in which a size 3/0 strand has the following combination of mechanical properties:
 Tensile strength—at least about 60,000 psi
 Knot strength—at least about 35,000 psi
 Young's modulus—less than 165,000 psi
 Elongation—from about 20% to 80%

3. The filament of claim 1 in which n is 4, and having a diameter of from about 0.01 to 1.0 mm.

4. A filament of claim 1 having a surgical needle attached to at least one end and useful as a surgical suture.

5. A filament of claim 1 in a sterile condition.

6. A woven or knitted surgical fabric comprised of filaments of claim 1.

7. A fabric of claim 1 in a seamless tubular construction.

8. A fibrillar surgical aid comprising knitted, woven or nonwoven filaments of claim 1.

9. A surgical suture package comprising a sterile enclosure and therein a sterile filament of claim 5.

10. A method of closing a wound in living tissue which comprises approximating and securing the wound tissue with a drawn and oriented, flexible thermoplastic surgical filament, comprising a copolymer consisting essentially of a multiplicity of random recurring A [poly(polymethylene terephthalate, isophthalate or cyclohexane-1,4-dicarboxylate)] and B [poly(polymethylene dimerate)] units having the following general formula:

$$+Z-O(CH_2)_nO\!\!+_{\overline{x}} \quad +C(O)\!\sim\!\!\overset{CH_3}{\underset{}{\phantom{X}}}\!\sim\!\!\overset{CH_3}{\underset{}{\phantom{X}}}\!\sim\!C(O)-O(CH_2)_n-O\!\!+_{\overline{y}}$$
$$\phantom{XXXXXX}A \phantom{XXXXXXXXXXXXXXXXXXX} B$$

wherein—Z—represents a member selected from the group consisting of $$-\overset{O}{\underset{}{C}}-\!\!\bigcirc\!\!-\overset{O}{\underset{}{C}}-, \quad -\overset{O}{\underset{}{C}}-\!\!\bigcirc\!\!-\overset{O}{\underset{}{C}}- \text{ and}$$

$$-\overset{O}{\underset{}{C}}-\!\!\bigcirc\!\!-\overset{O}{\underset{}{C}}-.$$

n is 4 to 8, x and y are numbers having average values such that the A units comprise 87 to 92 mole percent, and the B units comprise 13 to 8 mole percent of the copolymer, and denotes a branched hydrocarbon chain containing from 24 to 32 carbon atoms, in which a size 3/0 strand of said filament has the following combination of mechanical properties:
 Knot strength—at least about 35,000 psi
 Tensile strength—at least about 60,000 psi
 Young's modulus—between about 80,000 and 280,000 psi
 Elongation—from about 20% to 80%

* * * * *